US008834018B1

(12) United States Patent  
Kim (10) Patent No.: US 8,834,018 B1  
(45) Date of Patent: Sep. 16, 2014

(54) FAST RESPONSE MEASUREMENT STANDARDS

(75) Inventor: Mark Kim, Shoreline, WA (US)

(73) Assignee: The Boeing Company, Chicago, IL (US)

( * ) Notice: Subject to any disclaimer, the term of this patent is extended or adjusted under 35 U.S.C. 154(b) by 431 days.

(21) Appl. No.: 13/107,158

(22) Filed: May 13, 2011

(51) Int. Cl.  
*G01N 25/00* (2006.01)  
*G01N 25/70* (2006.01)

(52) U.S. Cl.  
USPC ............ 374/43; 374/179; 374/5; 374/57; 374/143; 374/153; 374/141; 374/46

(58) Field of Classification Search  
USPC .......... 374/4, 5, 11–12, 10, 29–39, 43–57, 374/100, 179, 141, 163, 185, 187, 194, 195, 374/205, 153, 143; 73/795, 787; 264/1.7, 264/406, 40.1, 228, 241  
See application file for complete search history.

(56) References Cited

U.S. PATENT DOCUMENTS

| | | | | | |
|---|---|---|---|---|---|
| 5,214,387 | A | * | 5/1993 | Fenner | 324/557 |
| 5,399,854 | A | * | 3/1995 | Dunphy et al. | 250/227.17 |
| 5,680,739 | A | * | 10/1997 | Cercone et al. | 52/741.3 |
| 6,056,436 | A | * | 5/2000 | Sirkis et al. | 374/161 |
| 6,137,573 | A | * | 10/2000 | Luke et al. | 356/453 |
| 6,231,796 | B1 | * | 5/2001 | Allen | 264/72 |
| 6,425,686 | B1 | * | 7/2002 | Zaldivar et al. | 374/16 |
| 6,876,785 | B1 | * | 4/2005 | Li et al. | 385/12 |
| 8,083,399 | B2 | * | 12/2011 | Werner et al. | 374/43 |
| 2002/0196994 | A1 | * | 12/2002 | Bosselmann et al. | 385/12 |
| 2003/0102070 | A1 | | 6/2003 | Black et al. | |
| 2008/0157437 | A1 | | 7/2008 | Nelson et al. | |
| 2009/0323757 | A1 | | 12/2009 | Werner et al. | |
| 2010/0038544 | A1 | | 2/2010 | Shelley et al. | |
| 2010/0155539 | A1 | | 6/2010 | Press | |
| 2010/0158069 | A1 | * | 6/2010 | Yoo et al. | 374/29 |
| 2011/0110396 | A1 | * | 5/2011 | Grayson et al. | 374/178 |
| 2011/0142091 | A1 | * | 6/2011 | Wardle et al. | 374/45 |
| 2012/0250726 | A1 | * | 10/2012 | Sorkine | 374/179 |

FOREIGN PATENT DOCUMENTS

| | | | |
|---|---|---|---|
| DE | 102008058882 A1 | * | 6/2010 |
| JP | 2003335876 A | * | 11/2003 |
| JP | 2004317372 A | * | 11/2004 |

* cited by examiner

*Primary Examiner* — Gail Verbitsky  
(74) *Attorney, Agent, or Firm* — Hope Baldauff, LLC (57) ABSTRACT

This disclosure is directed to apparatuses, systems, and methods that can quickly and reliably determine a stationary or non-stationary change in temperature. During a simulated test of, for example, the heater system of an automated and/or high-speed composite material placement machine may be evaluated at any single location along a course whether a lay down material is heated below, at, or beyond its particular temperature requirements. Temperature measurements can be of a heat source that is moving at a rate from zero to over 3000 inches/minute. Temperature measurements of a moving heat source are reliable within a variance of approximately plus or minus 3° F. In addition, temperature measurements of a moving heat source on a laminated material may be had with a plurality of sensors along at least one direction and to various depths.

15 Claims, 9 Drawing Sheets

FAST RESPONSE MEASUREMENT STANDARDS

BACKGROUND

Auto-lamination machines or composite material placement machines (collectively "CMPM") lay down individual or multiple strips of uncured pre-impregnated composite material by dispensing these strips out mechanically, and providing compaction pressure and heat to promote adherence against the tool or part surface. Examples of these technologies include automated fiber placement, automated tape laying, and filament winding. The use of compaction pressure and heat has increased with the desire to increase manufacturing productivity and laydown rates in high-speed CMPMs. Existing high-speed CMPMs and integrated heater systems can travel upwards of 2400 inches per minute during laydown.

The composite materials most often used in high-performance aerospace applications include a reinforcement and an epoxy based resin, which is typically sensitive to temperature exposure. There are presently two primary types of heater system technologies used with CMPMs, heated compressed air and infrared bulbs. Typically the infrared type heat source is configured to emit a wavelength of electromagnetic radiation that is absorbed by the resin to a relatively greater extent than the wavelength of electromagnetic radiation is absorbed by the reinforcement.

Both heater systems direct the heat towards the substrate or layup surface near or just ahead of the compaction point. This layup surface is often the previous layer or layers of composite material. Higher than desired temperature exposure to a previous layer or layers could result in premature cross-linking within the resin system, which could negatively effect mechanical properties of the composite material.

Various temperature measurement techniques have been attempted or are utilized. These include the use of non-contacting devices such as pyrometers and thermographic cameras, as well as the use of contact devices such as temperature sensitive films. Obstacles associated with the use of pyrometers and thermographic cameras include a sensitivity to reflected light and a dependency on the emissivity of the measured surface, and the need for line-of-sight. Infrared based heater systems often produce a bright reflection off the heated surface, resulting in artificially high temperature measurements when using pyrometers or thermographic cameras. Additionally, direct line-of-sight is typically not achievable due to machine geometry. Obstacles associated with temperature sensitive films include their inherent differences in emissivity, heat transfer properties, and lack of responsiveness.

SUMMARY

It should be appreciated that this Summary is provided to introduce a selection of concepts in a simplified form that are further described below in the Detailed Description. This Summary is not intended to be used to limit the scope of the claimed subject matter.

One embodiment of the present disclosure is directed to a fast response measurement apparatus, which includes a base to which a material specimen having at least two layers of composite material is positioned. To the material specimen is attached at least one sensor configured to measure the effect of an action to the material specimen, such as the change in temperature of a moving heat source during a simulated test run. The sensor may be positioned on the top layer of fiber reinforced plastic, and additional sensors may be placed on other layers. A sensor connector is operatively connected to the sensor.

Another embodiment of the present disclosure is directed to a fast response measurement system, having at least one fast response measurement apparatus that includes a base to which a material specimen having at least two layers of composite material is positioned. To the material specimen is attached at least one sensor configured to measure the effect of an action to the material specimen, such as the change in pressure of a moving compaction roller during a simulated test run. The sensor may be positioned on the top layer of fiber reinforced plastic, and additional sensors may be placed on other layers. A sensor connector is operatively connected to the sensor and to a data acquisition unit. To the data acquisition unit is operatively connected a computer.

Yet another embodiment of the present disclosure provides methods for the testing of a composite material placement machine. Operations associated with one routine include determining at least a portion of a composite material lay down course and determining at least one measurement location along the lay down course. At least one fast response test apparatus is placed at the measurement location, causing the composite material placement machine to execute at least a portion of the composite material lay down course. The first response test apparatus captures the performance measurements of the composite material placement machine and monitors the performance measurements of the composite material placement machine.

The features, functions, and advantages that have been discussed can be achieved independently in various embodiments of the present disclosure or may be combined in yet other embodiments, further details of which can be seen with reference to the following description and drawings.

DETAILED DESCRIPTION

Figure 1:
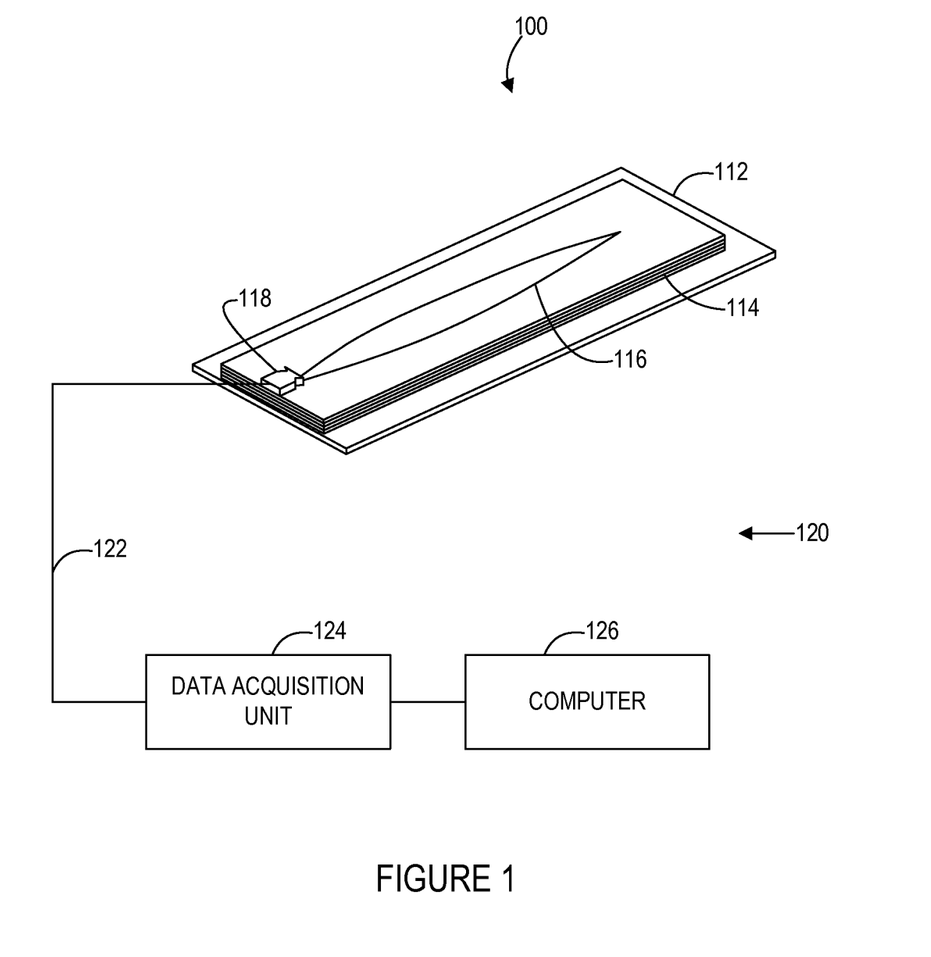
FIG. 1 illustrates an exemplary fast response measurement apparatus (FRMA) and fast response measurement system (FRMS).

Turning now to FIG. 1, there is illustrated an exemplary fast response measurement apparatus (FRMA) 100. For the present purposes of illustration and teaching, and not restriction or limitation, this FRMA 100 is configured to measure temperature with a single sensor at a single location within the context of an auto-lamination machine or a composite material placement machine (collectively "CMPM"). A contemporary CMPM may be a robotic armature or gantry-type positioning device configured to control three to ten or more axes of movement. The rate of movement for a CMPM may be in any one of the following ranges: less than 50 inches/minute; 50-500 inches/minute; 500-1000 inches/minute; 1000-2000 inches/minute; and more than 2000 inches/ minute. An advantage of the present disclosure is that embodiments of a FRMA 100 are adaptable to various rates of movement.

Generally speaking, a composite material includes a reinforcement and a resin. The reinforcement may comprise, for example, fabric, tape, film, foil, fibers, combinations thereof, and the like. Fibers may comprise, for example, carbon, boron, aramid, quartz, combinations thereof, and the like. The resin may comprise thermoset and thermoplastic resins. Thermoset resins include epoxy, polyurethane polyester, phenolic resins, vinyl ester and polyimide resins, combinations thereof, and the like. Thermoplastic resins may comprise, for example, acetal resins, polypropylene, polycarbonate, nylon, combinations thereof, and the like. To facilitate adhesion of the composite material to a form, substrate, or other ply(s) the CMPM may include a heater and compaction roller. Here the terms "ply" and "layer" are fully interchangeable, whether in the singular or plural.

The heater of a CMPM is configured to soften and increase the tack of the resin while the compaction roller of a CMPM is configured to urge the composite material upon the form or a substrate. The heater temperature is typically determined by an algorithm, which is usually dependent on the heater head speed. Accordingly, the FRMA 100 of FIG. 1 may be used to accurately measure rapidly moving temperature; that is, the heat of the CMPM heater output as the heater head quickly passes over a particular location. In another embodiment, a FRMA 100 may be configured to accurately measure a rapidly moving force, that is, the force of the CMPM compaction roller as it quickly presses composite material over a particular location.

In other embodiments, a FRMA 100 can measure a variety of characteristics, traits, actions, effects, or standards within a variety of applications or environments. For example, in addition to temperature and pressure, a FRMA 100 may be configured with a sensor(s) or gauge(s) to measure the effect of an action to a material specimen such as force, impact, stress, strain, bending, elasticity, light reflection, conductivity, combinations thereof, and the like. Embodiments of a FRMA 100 may be applied to or within the context of manufacturing, processing, distributing, calibrating, testing, combinations thereof, and the like.

The illustrated FRMA 100 comprises a base 112 of pre-cured composite laminate. The base of the exemplary FRMA 100 is constructed of approximately 24 plys of carbon fiber reinforced plastic (CFRP), each approximately 0.0075" thick for a total thickness of approximately two inches (2"). Other embodiments may have more or less plys of greater or lesser thicknesses. On the base 112 is attached a material specimen 114. Here the material specimen 114 is approximately 5 plys of pre-impregnated, uncured, pre-consolidated CFRP. Other embodiments may comprise material of more or less plys of greater or lesser thicknesses, may not be pre-impregnated, and may be cured.

To the illustrated material specimen 114 is attached a sensor. For the purposes of this disclosure and teaching, a sensor includes a device configured to measure the effect of an action to the material specimen. Examples of an effect of an action to the material specimen include the change in temperature of a moving heat source and a change in pressure of a moving compaction roller, mostly probably but not necessarily during a simulated test run. Additional examples of an effect of an action to the material specimen include measuring the effects of force, impact, stress, strain, bending, elasticity, light reflection, conductivity, combinations thereof, and the like.

In the embodiment illustrated in FIG. 1 the sensor is in the form of a thermocouple 116. An example of a thermocouple 116 suitable for the illustrated embodiment is an Omega® brand type K fine gauge thermocouple (now or formally Model No. CHAL-005). Other unsheathed fine gage microtemp thermocouples are contemplated and may be used, including type J, T, E, and the like. To the thermocouple 116 is connected a sensor connector in the form of a thermocouple connector 118. An example of a thermocouple connector 118 suitable for the illustrated embodiment is an Omega® brand type K miniature connector (now or formally Model No. NMP-K-(MF). Other thermocouple connectors are contemplated and may be used. An advantage of the illustrated FRMA 100 is that it can accurately measure a rapidly moving change in temperature within a range of approximately plus or minus 3° F.

An exemplary method of handcrafting a FRMA 100 according to one embodiment will now be described for illustrative purposes. It should be appreciated that more or fewer operations may be performed than described herein and in a different order than the order described herein. Moreover, it should be appreciated that the precise specifications discussed with respect to this example, such as materials, number of plys, dimensions, and pressures, are indicative of one illustrative embodiment only, and are not intended to be limiting. According to this example, a quasi-isotropic CFRP laminate panel is first fabricated to be the base 112. This panel may be of hand layup and autoclave cured, of approximately 16 or more plys. To the base 112 is applied adhesive or double sided tape, to which is stacked and pressure compacted a material specimen 114. Here the material specimen 114 comprises 5 plys of pre-impregnated, uncured CFRP, each of which are individually pressure compacted using, for example, an elastomeric vacuum table. To the top of the material specimen 114 is attached the thermocouple 116, which may be secured using adhesive or high temperature polyester tape. To the base 112 or material specimen 114 is attached the thermocouple connector 118, which may be secured using adhesive or double sided tape. A pre-cut uncured segment of CFRP may be placed just before the thermocouple junction so that the junction remains uncovered by the tape.

A Teflon coated aluminum tab is placed directly over the thermocouple junction. This Teflon coated aluminum tab may be 0.25" thick by 1" square. With these elements in place and positioned on the elastomeric vacuum table, close the lid and apply a vacuum of approximately 14.7 psi. Using a heat source, such as a heat gun, heat the aluminum tab through the elastomeric rubber. The conductive heat from the aluminum tab will soften the CFRP, allowing the thermocouple junction to drop into the top ply of the uncured material specimen 114. This method concludes with the operations of allowing the vacuum table to reach room temperature, removing the vacuum and removing the FRMA 100. An advantage of embedding the thermocouple junction in the uncured material specimen 114 is a more accurate measurement of the temperature of the CFRP heat source at a particular level of ply or course material.

FIG. 1 also illustrates a fast response measurement system (FRMS) 120. The illustrated FRMS 120 comprises a FRMA 100 operatively connected to a computer 126 via a data acquisition unit 124 and a sensor extension cable 122. According to various implementations, the data acquisition unit 124 and computer 126 of the FRMS 120 are operative to collect and analyze data, respectively, from the FRMA 100 during the manufacture of composite materials. An example of one sensor extension cable 122 suitable for the illustrated embodiment is an Omega® brand type K extension wire (now or formally Model No. GECK25-8). Any sensor extension cable 122 compatible with the sensor connector is contemplated and may be used. The sensor extension cable 122 is operatively connected to a data acquisition unit 124. An example of one data acquisition unit 124 suitable for the illustrated embodiment is an Agilent® brand data acquisition unit (now or formally Model No. 34970A). Any compatible data acquisition unit 124 is contemplated and may be used. The data acquisition unit 124 is operatively connected to a standard computer 126 comprising compatible Agilent® software instructions that receive data from the FRMA 100 through the data acquisition unit 124. Alternative embodiments of a FRMS 120 provides for wireless communication between the FRMA 100 and data acquisition unit 124. Accordingly, in that embodiment a transceiver (not shown), for example, may be operatively attached to the thermocouple 116 and in communication with the data acquisition unit 124, and the sensor extension cable 122 may be eliminated.

Any brand of computer 126 and software compatible with the respective data acquisition unit 124 is contemplated and may be used. The computer 126 includes any device capable of executing the software components configured to receive and process data from the data acquisition unit 124. Thus, the computer 126 includes devices such as but not limited to a server computer, a desktop computer, a netbook computer, a tablet computer, and/or a laptop computer, combinations thereof, and the like. A typical computer 126 includes a central processing unit (CPU), a system memory including a random access memory (RAM) and a read-only memory (ROM), and a system bus that couples the memory to the CPU. A basic input/output system containing the basic routines that help to transfer information between elements within the computer architecture, such as during startup, is stored in the ROM. The computer 126 further includes a mass storage device for storing the operating system.

The mass storage device is connected to the CPU through a mass storage controller connected to the bus. The mass storage device and its associated computer-readable media provide non-volatile storage for the computer 126. Although the description of computer-readable media contained herein refers to a mass storage device, such as a hard disk or CD-ROM drive, it should be appreciated that computer-readable media can be any available computer storage media or communication media that can be accessed by the computer architecture.

Communication media includes computer readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

By way of example, and not limitation, computer storage media may include volatile and non-volatile, removable and non-removable media implemented in any method or technology for storage of information such as computer-readable instructions, data structures, program modules or other data. For example, computer media includes, but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage or other magnetic storage devices, or any other medium which can be used to store the desired information and which can be accessed by the computer architecture. For purposes of the claims, the phrase "computer storage medium" and variations thereof, does not include waves, signals, and/or other transitory and/or intangible communication media, per se.

An advantage of an embodiment of the present disclosure includes a FRMS 120 that can quickly and reliably determine and evaluate during a simulated test, for example, the heater system of an automated and/or high-speed CMPM at any single location along a course, whether a lay down material is heated below, at, or beyond its particular temperature requirements. An advantage of another embodiment of the present disclosure includes a FRMS 120 that is portable. Another advantage of an embodiment of the present disclosure includes a FRMS 120 that is reliable within a variance or range of approximately plus or minus 3° F. Moreover, the present disclosure provides an advantageous method of testing and determining the temperature of the heat applied to the composite material at a particular location along the course of a CMPM lay down.

Figure 2A:
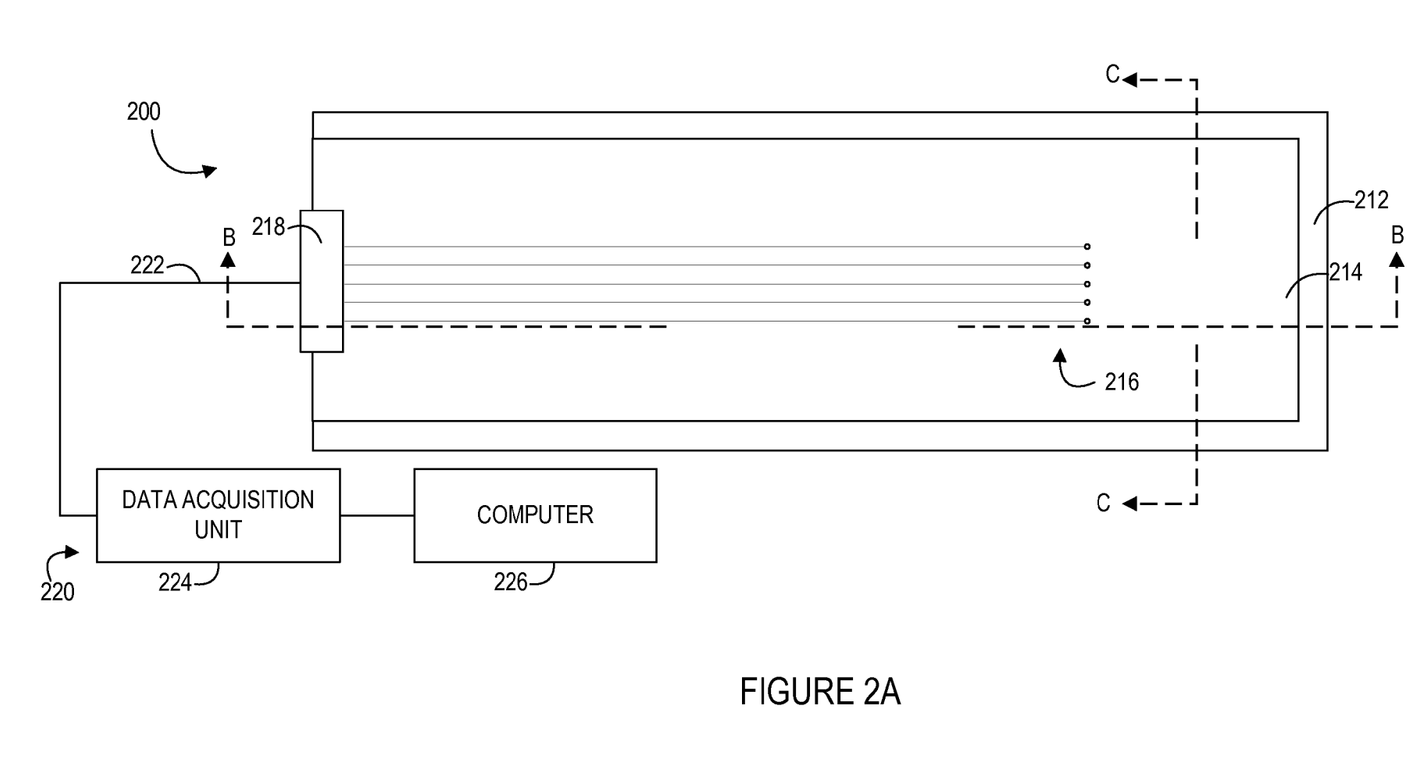
FIGS. 2A-2C illustrates a plan and cross-sectional views of an exemplary FRMA and FRMS.
Figure 2B:
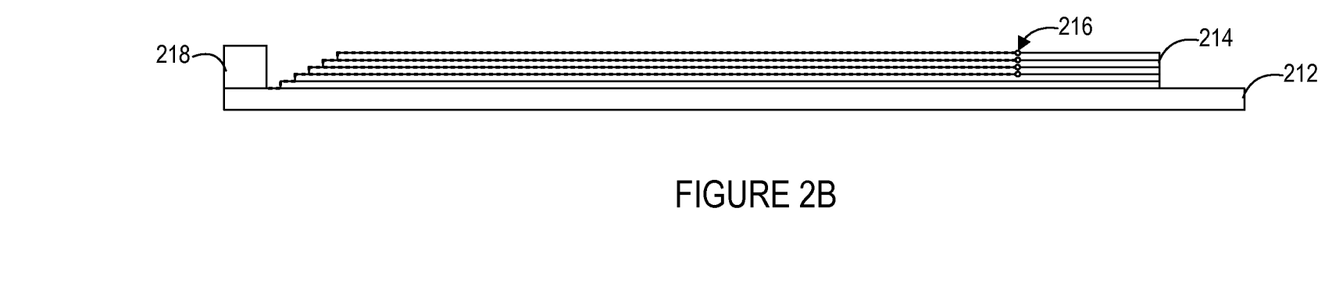
Figure 2C:
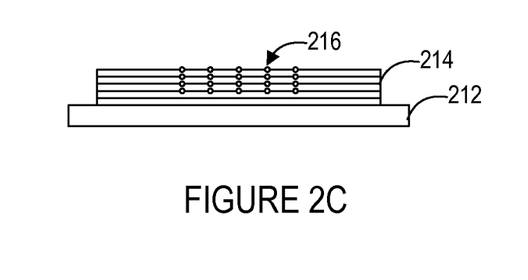

Turning now to FIGS. 2A-2C, there is illustrated another exemplary FRMA 200. FIG. 2B shows a cross-sectional view taken along lines B-B of the FRMA 200 shown in FIG. 2A. FIG. 2C shows a cross-sectional view taken along lines C-C of the FRMA 200 shown in FIG. 2A. For the present purposes of illustration and teaching, and not restriction or limitation, this FRMA 200 is configured to measure temperature with a plurality of sensors along a first predetermined course of orientation or direction and to various depths. Similar to the FRMA 100 described above with reference to FIG. 1, the FRMA 200 of FIG. 2 comprises a base 212 of precured composite laminate and on the base 212 is attached a material specimen 214 constructed of five (5) plys of composite material.

To the material specimen 214 is attached a plurality of sensors in the form of thermocouples 216. As shown in FIGS. 2A-2C, five (5) thermocouples 216 are collinearly arranged along the top ply, and five (5) thermocouples 216 are likewise collinearly arranged along each of the lower three (3) plys for a total of twenty (20) thermocouples 216 included in the illustrated embodiment. However, any number of thermocouples 216 may be arranged along any number of plys and in any pattern. By way of example and not limitation, in an alternative embodiment four (4) thermocouples 216 may be arranged along the top ply, ten (10) thermocouples 216 may be arranged along the next lower ply, seven (7) thermocouples 216 may be arranged along the next lower ply, no thermocouples 216 may be arranged along the next lower ply, twenty-six (26) thermocouples 216 may be arranged along the next lower ply, combinations thereof, and the like. To the thermocouples 216 is connected at least one sensor connector in the form of a thermocouple connector 218. The FRMA 200 may be constructed according to the methods described above.

FIG. 2A also illustrates a FRMS 220. The illustrated FRMS 220 comprises a FRMA 200 operatively connected to a sensor extension cable 222. The sensor extension cable 222 is operatively connected to a data acquisition unit 224, which is operatively connected to a standard computer 226. The computer 226 comprises compatible software instructions that may provide test results, provide real-time data displays, and provide analyses of information received from the FRMA 200 through the data acquisition unit 224.

An advantage of an embodiment of the present disclosure includes a FRMS 220 that can test, for example, the uniformity of a heater system as the heater head accelerates at the start of the course and as it runs its course. In this way, there may be evaluated along various points of a first orientation whether a lay down material is heated below, at, or beyond its particular temperature requirements. An advantage of an embodiment of the present disclosure includes a FRMS 220 that can test, for example, the heater system of an automated and/or high-speed CMPM and evaluate along various depths of a first orientation to determine whether the previous lay down material is heated below, at, or beyond its particular temperature requirements. In this regard, the effect of repeated heat exposure on the lower plys may be evaluated. Accordingly, an advantage of the present disclosure includes a method of testing and determining the temperature applied to the composite material at points along the surface and depth of a CMPM lay down a path or course.

Figure 3A:
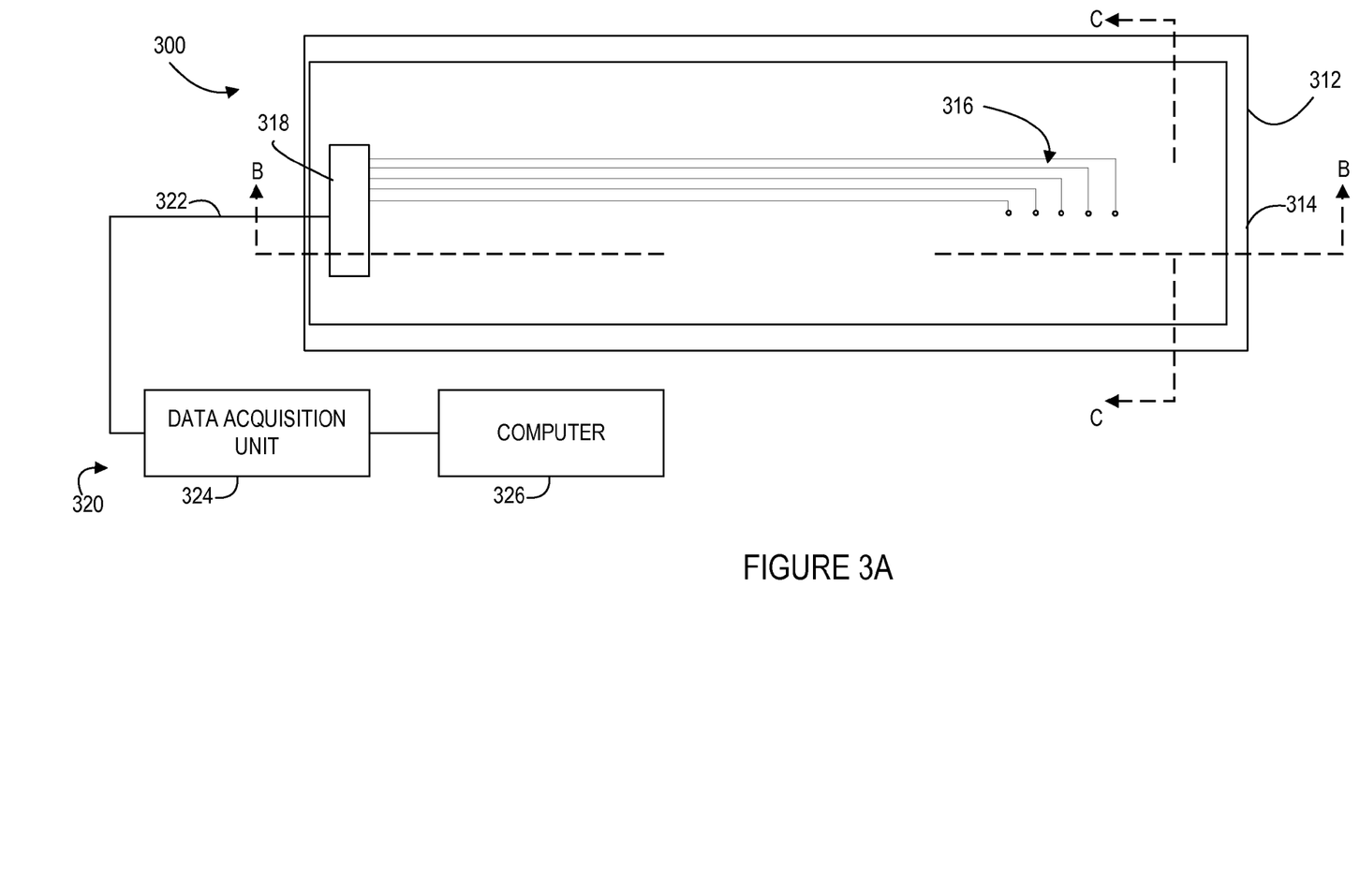
FIGS. 3A-3C illustrates a plan and cross-sectional views of an exemplary FRMA and FRMS.
Figure 3B:
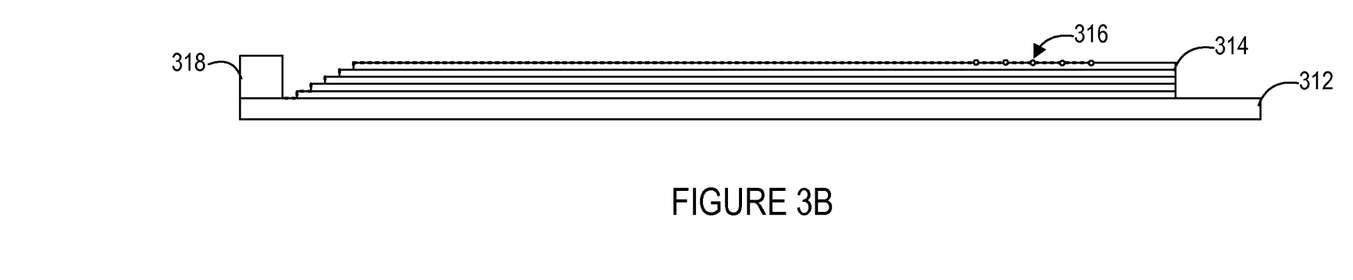
Figure 3C:
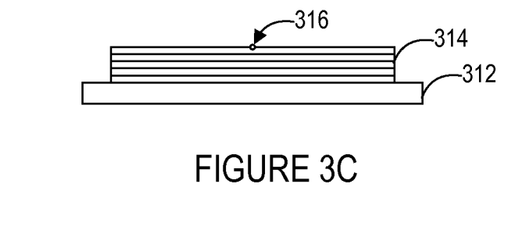

Turning now to FIGS. 3A-3C, there is illustrated another exemplary FRMA 300. FIG. 3B shows a cross-sectional view taken along lines B-B of the FRMA 300 shown in FIG. 3A. FIG. 3C shows a cross-sectional view taken along lines C-C of the FRMA 300 shown in FIG. 3A. For the present purposes of illustration and teaching, and not restriction or limitation, this FRMA 300 is configured to measure temperature with a plurality of sensors along a second predetermined course of orientation or direction. Similar to the FRMA 100 described above with reference to FIG. 1, the FRMA 300 of FIGS. 3A-3C comprises a base 312 of precured composite laminate and on the base 312 is attached a material specimen 314 constructed of five (5) plys of composite material.

To the material specimen 314 is attached a plurality of sensors in the form of thermocouples 316. As shown in FIG. 3, five (5) thermocouples 316 are collinearly arranged along the top ply. To the thermocouples 316 is connected at least one sensor connector in the form of a thermocouple connector 318. The FRMA 300 may be constructed according to the methods described above.

FIGS. 3A-3C also illustrates a FRMS 320. The illustrated FRMS 320 comprises a FRMA 300 operatively connected to a sensor extension cable 322. The sensor extension cable 322 is operatively connected to a data acquisition unit 324, which is operatively connected to a standard computer 326. The computer 326 comprises compatible software instructions that may provide test results, provide real-time data displays, and provide analyses of information received from the FRMA 300 through the data acquisition unit 324.

An advantage of an embodiment of the present disclosure includes a FRMS 320 that can test, for example, the uniformity of a heater system as the heater head accelerates at the start of the course and as it runs its course. In this way there may be evaluated along various points of a second orientation whether a lay down material is heated below, at, or beyond its particular temperature requirements.

Figure 4A:
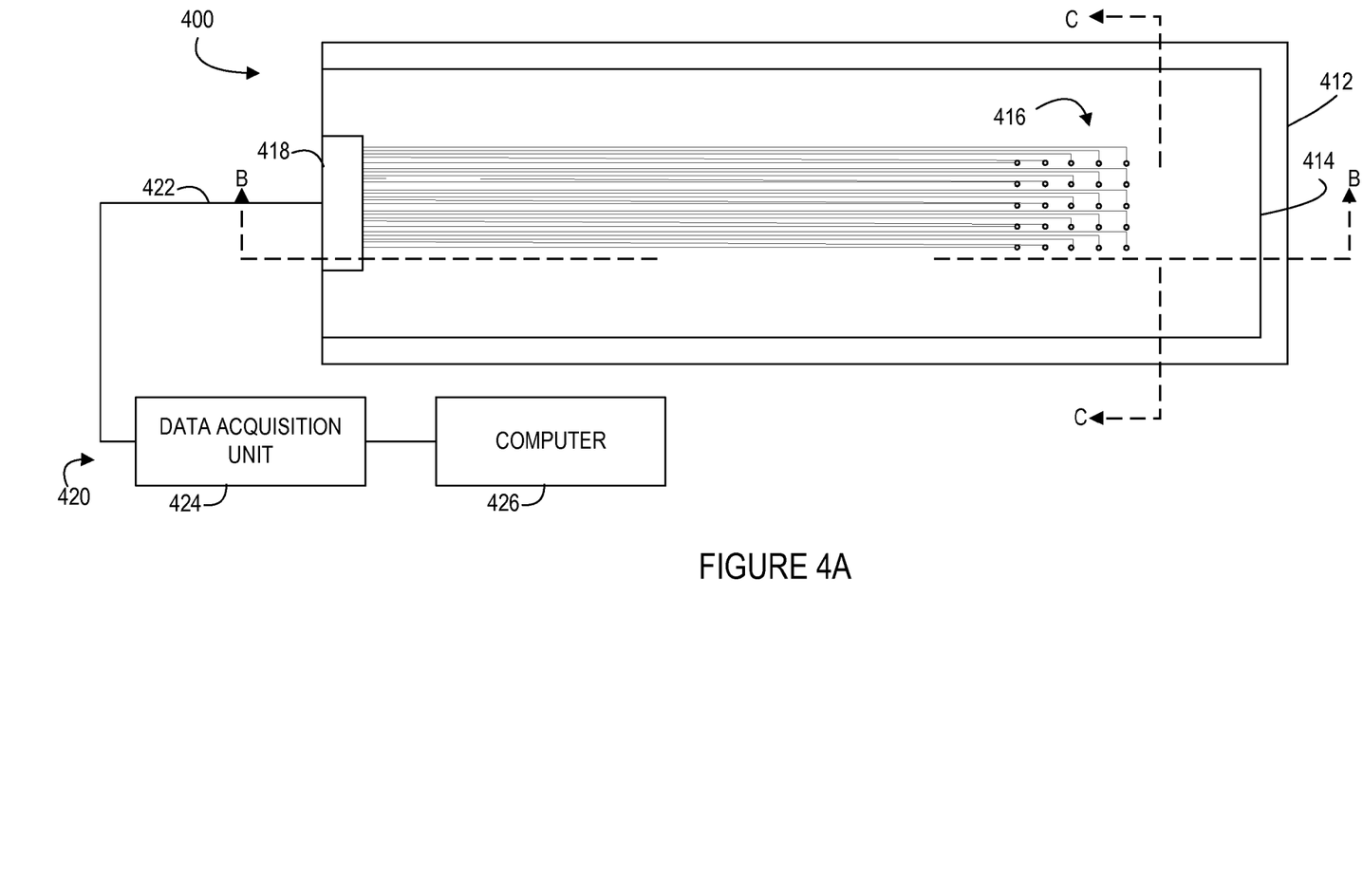
FIGS. 4A-4C illustrates a plan and cross-sectional views of an exemplary FRMA and FRMS.
Figure 4B:
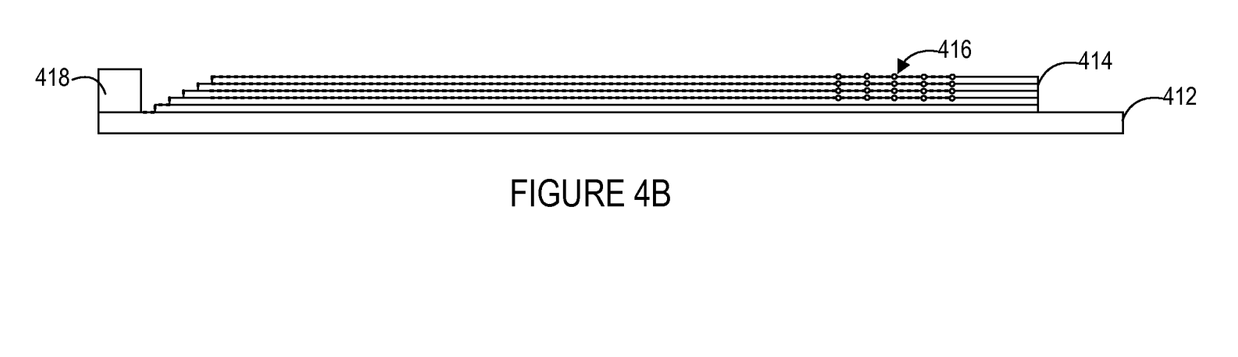
Figure 4C:
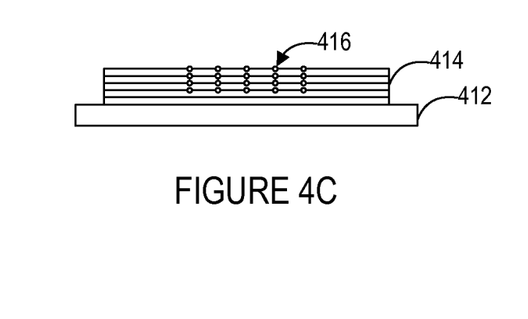

Turning now to FIGS. 4A-4C, there is illustrated another exemplary FRMA 400. FIG. 4B shows a cross-sectional view taken along lines B-B of the FRMA 400 shown in FIG. 4A. FIG. 4C shows a cross-sectional view taken along lines C-C of the FRMA 400 shown in FIG. 4A. For the present purposes of illustration and teaching, and not restriction or limitation, this FRMA 400 is configured to measure temperature with a plurality of sensors along a plurality of courses of orientation or direction over an area, and to a plurality of depths. Similar to the FRMA 100 described above with reference to FIG. 1, the FRMA 400 of FIGS. 4A-4C comprises a base 412 of precured composite laminate and on the base 412 is attached a material specimen 414 constructed of five (5) plys of composite material.

To the material specimen 414 is attached a plurality of sensors in the form of thermocouples 416. As shown in FIGS. 4A-4C, twenty-five (25) thermocouples 416 are arranged within the top ply, and twenty-five (25) thermocouples 416 are likewise arranged within each of a plurality of the underlying plys for a total of one hundred (100) thermocouples throughout this material specimen 414. However, any number of thermocouples 416 may be arranged along any number of plys and in any pattern. By way of example and not limitation, in an alternative embodiment thirty-two (32) thermocouples 416 may be arranged along the top ply, seventeen (17) thermocouples 416 may be arranged along the next lower ply, no thermocouples 416 may be arranged along the next lower ply, forty-four (44) thermocouples 416 may be arranged along the next lower ply, nine (9) thermocouples 416 may be arranged along the next lower ply, combinations thereof, and the like. To the thermocouples 416 is connected at least one sensor connector in the form of a thermocouple connector 418. The FRMA 400 may be constructed according to the methods described above.

FIGS. 4A-4C also illustrates a FRMS 420. The illustrated FRMS 420 comprises a FRMA 400 operatively connected to a sensor extension cable 422. The sensor extension cable 422 is operatively connected to a data acquisition unit 424, which is operatively connected to a standard computer 426. The computer 426 comprises compatible software instructions that may provide test results, provide real-time data displays, and provide analyses of information received from the FRMA 400 through the data acquisition unit 424.

An advantage of an embodiment of the present disclosure includes a FRMS 420 that can test, for example, the uniformity of a heater system of an automated and/or high-speed CMPM as the heater head accelerates, decelerates, stops, and starts along a course and as it runs its course. In this way there may be evaluated along various points of any orientation, along the top layer and/or lower layers, whether a lay down material is heated below, at, or beyond its particular temperature requirements. In this regard, the effect of repeated heat exposure on the lower layers may also be evaluated. Accordingly, an advantage of the present disclosure includes a method of testing and determining the temperature of the heat applied to the composite material at particular points along the surface and depth of a path or course of a CMPM lay down.

Figure 5:
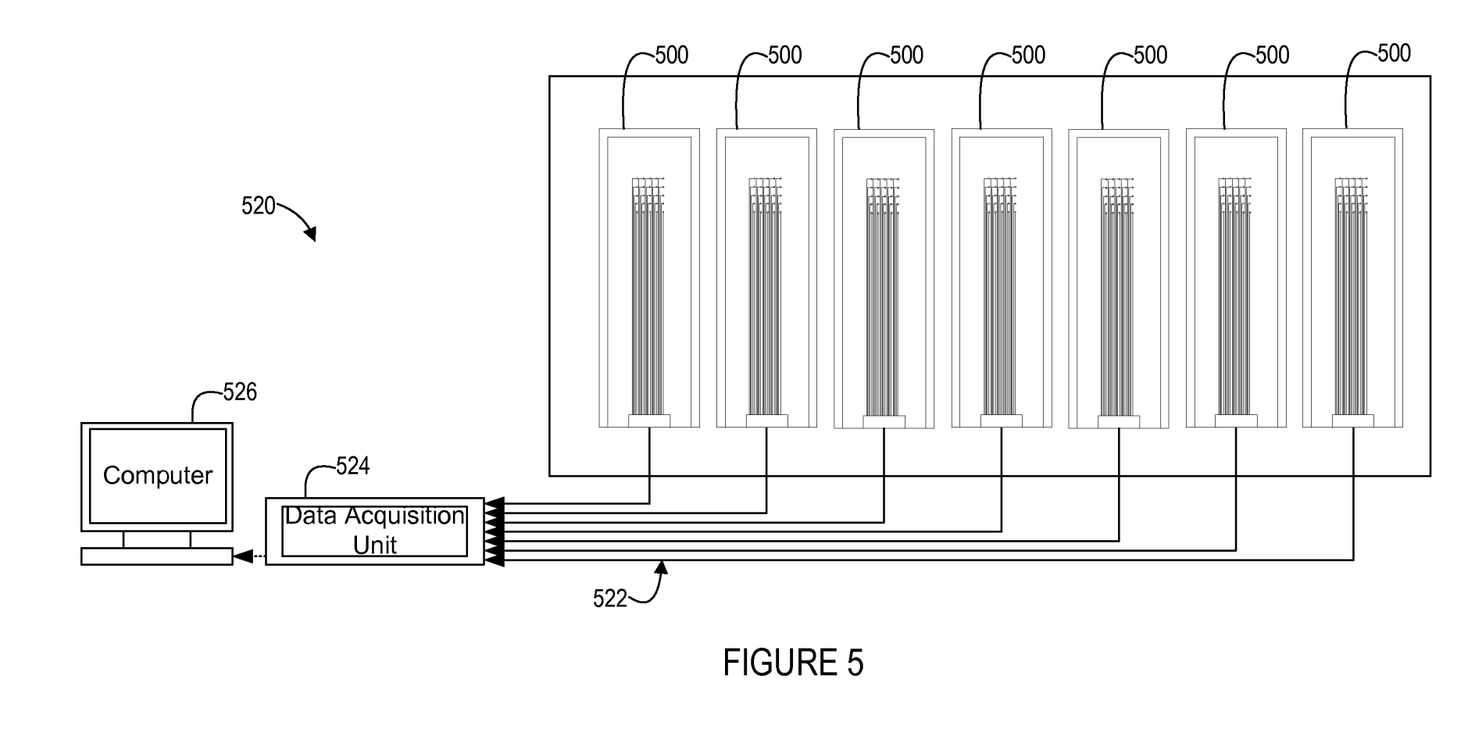
FIG. 5 illustrates a plan view of an exemplary FRMA and FRMS.

Turning now to FIG. 5, there is illustrated a plurality of FRMAs 500 arranged in a pattern suitable for testing the temperature of a heater system as the heater head moves across a broad area. The FRMAs 500 may be similar to the embodiments described above, combinations thereof, and the like. The FRMS 520 comprises the plurality of FRMAs 500, each operatively connected to a sensor extension cable 522. The sensor extension cable 522 is operatively connected to a data acquisition unit 524, which is operatively connected to a standard computer 526. The computer 526 comprises compatible software instructions that may provide test results, provide real-time data displays, and provide analyses of information received from the FRMAs 500 through the data acquisition unit 524.

An advantage of an embodiment of the present disclosure includes a FRMS 520 that can test, for example, the uniformity of a heater system of an automated and/or high-speed CMPM as the heater head accelerates, decelerates, stops, and starts along a course and as it runs its course. In this way there may be evaluated along various points of any orientation, along the top layer and or layer layers, whether a lay down material is heated below, at, or beyond its particular temperature requirements. In this regard, the effect of repeated heat exposure on the lower layers may also be evaluated. Accordingly an advantage of the present disclosure includes a method of testing and determining the temperature of composite material at particular points along the surface and depth of a path or course of a CMPM lay down.

Figure 6:
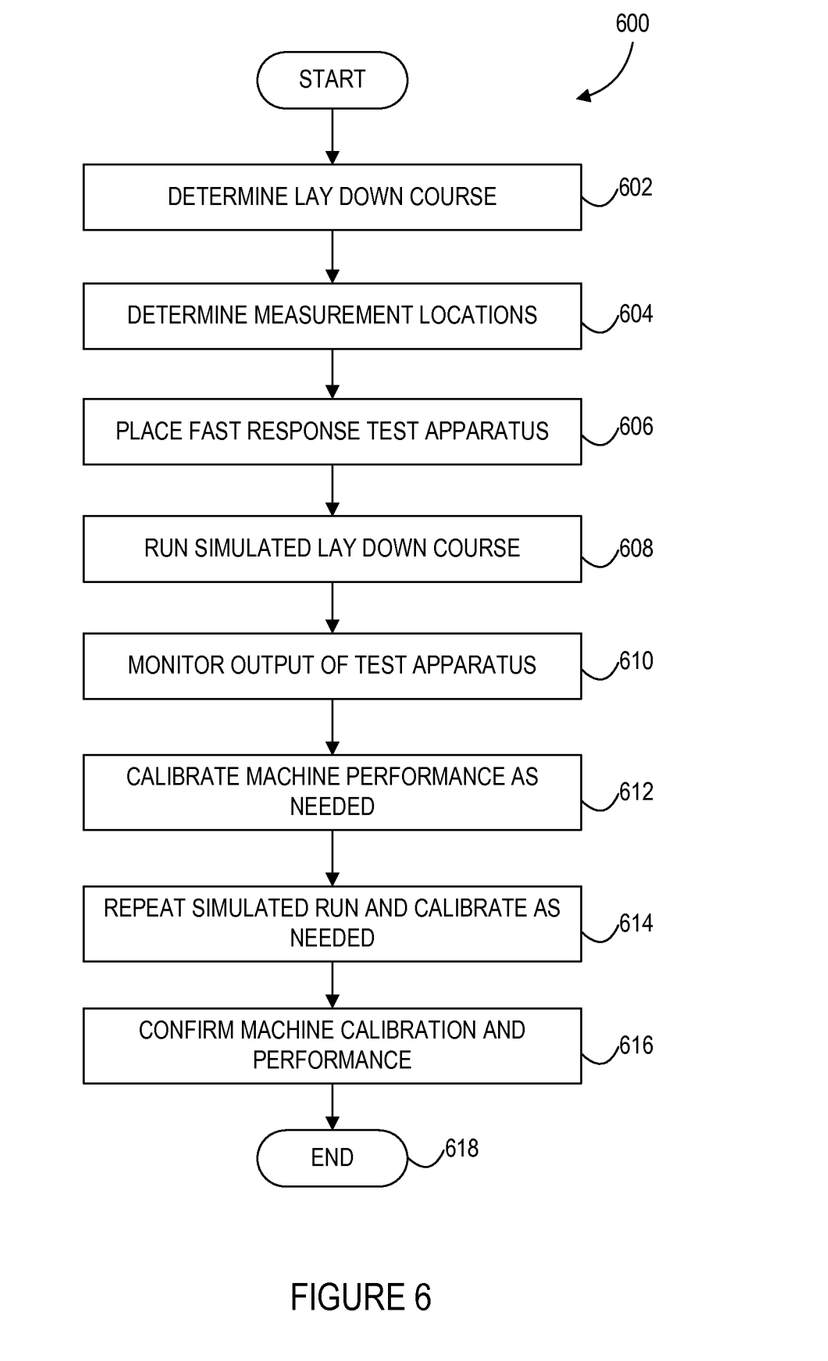
FIG. 6 illustrates a flow chart directed to an exemplary method of testing and calibrating a machine using a FRMA and FRMS.

Turning now to FIG. 6, an illustrative routine 600 for an exemplary method of testing and/or calibrating the heater system of an automated and/or high-speed CMPM during a simulated lay down course using a FRMS will now be described. It should be appreciated that more or fewer operations may be performed than shown in FIG. 6 and described herein. Moreover, these operations may also be performed in a different order than the order described herein.

The routine 600 begins at operation 602 with determining a lay down course. The lay down course is most typically the combination of paths or directions the heater head of the CMPM is programmed to execute. Along the lay down course the heater head will typically execute one or more of the following programmed commands: start, move in a first direction, accelerate, travel at a constant speed, decelerate, stop, restart, move in a second direction, combinations thereof, and the like.

The routine 600 continues from operation 602 to operation 604 with determining measurement locations along the lay down course. Selection of the measurement locations may be determined by whatever design criteria is required of the composite material; the CMPM itself; certification of the CMPM; manufacturing, operations, or processing demands; combinations therefore, and the like. For example, for the purposes of certifying a CMPM after delivery and setup, it may be helpful to determine the temperature output of a heater head when it has stopped. One reason for measuring the temperature at the location of a stop is that because of residual heat buildup the actual heater head temperature and therefore the temperature output may be greater than the programmed temperature.

The routine 600 continues from operation 604 to operation 606 with placing the fast response measurement apparatus (FRMA) at measurement locations. One or more embodiments of a FRMA may be placed at each measurement location. This operation may include placing one or more FRMAs between measurement locations. The routine 600 continues from operation 606 to operation 608 with running a simulated lay down course. In this operation the CMPM is run such that the heater head is directed through the lay down course and at the operating temperature required for the particular lay down course.

The routine 600 continues from operation 608 to operation 610 with monitoring the output of the test apparatus. This operation may include sending to the data acquisition unit the measurements acquired from the FRMAs. This operation may also include sending from the data acquisition unit to the computer the measurements acquired from the FRMAs. This operation may also include the computer analyzing and reporting the measurements acquired from the FRMAs.

The routine 600 continues from operation 610 to operation 612 with calibrating the performance characteristics of the CMPM in response to the results of the simulated lay down course. This operation may include recalibrating or otherwise adjusting the temperature output of the heater system, or the speed of the heater head to avoid excessive heat exposure to one or more plys of the composite material. The routine 600 continues from operation 612 to operation 614 with repeating a simulated lay down course as described in operation 608. This operation 614 may include replacing one or more FRMAs with a FRMA having an uncured material specimen before repeating a simulated lay down course. This operation 614 may likewise include repeatedly executing a simulated lay down course.

The routine 600 continues from operation 614 to operation 616 with confirming the CMPM is properly calibrated and performing according to design criteria. This operation 616 may include certifying the CMPM or a component, such as the heater system.

The subject matter described above is provided by way of illustration only and should not be construed as limiting. Various modifications and changes may be made to the subject matter described herein without following the exemplary embodiments and applications illustrated and described, and without departing from the true spirit and scope of the present disclosure, which is set forth in the following claims.

What is claimed is:

1. A measurement system for measuring characteristics of a composite material placement machine (CMPM) for laying down at least two layers of a composite material, the system comprising:
   a component of the CMPM configured to have an effect upon the at least two layers while forming the composite material;
   a simulated lay down course configured to simulate laying down the at least two layers of the composite material, the component of the CMPM configured for following the simulated lay down course;
   a measurement apparatus placed on the CMPM along the simulated lay down course, the measurement apparatus comprising an uncured material specimen of the at least two layers of the composite material; and
   at least one sensor positioned on the material specimen of the measurement apparatus, the at least one sensor configured to measure the effect of an action of the component of the CMPM to the uncured material specimen while the component follows the simulated lay down course, and wherein the CMPM may be calibrated for laying down the at least two layers to form the composite material based upon the effect of the action of the component of the CMPM to the material specimen.

2. The measurement system of claim 1, wherein the component is a heater head and the at least one sensor measures a temperature of the material specimen as the heater head passes over the measurement apparatus.

3. The measurement system of claim 1, wherein the component is a compaction roller and the sensor measures changes in pressure on the material specimen as the compaction roller passes over the measurement apparatus.

4. The system of claim 1, wherein the measurement apparatus further comprises a base configured to receive the uncured material specimen and the base is precured.

5. The system of claim 1, wherein the at least two layers of composite material further comprises pre-impregnated, uncured fiber reinforced plastic.

6. The system of claim 5, wherein the at least one sensor is embedded in a layer of the at least two layers of pre-impregnated, uncured fiber reinforced plastic.

7. The system of claim 1, wherein the at least one sensor comprises a thermocouple configured to measure a change in temperature.

8. The system of claim 7, wherein the thermocouple is configured to measure a change in temperature within a range of less than approximately 3° F.

9. The system of claim 7, wherein the thermocouple is configured to accurately measure a change in temperature while the component of the CMPM moves at a rate of at least approximately 50 inches per minute.

10. The system of claim 1, further comprising a plurality of sensors positioned on a second layer of composite material and configured to measure the effect of an action to the material specimen.

11. The system of claim 1, further comprising a third layer of composite material having positioned thereon a plurality of sensors configured to measure the effect of an action to the material specimen.

12. The system of claim 1, further comprising:
   a data acquisition unit operatively connected to the sensor; and,
   a computer operatively connected to the data acquisition unit.

13. The system of claim 12, wherein the at least one sensor is configured to measure temperature, force, impact, stress, strain, bending, elasticity, light, moisture, or conductivity.

14. The system of claim 12, wherein the data acquisition unit is configured to receive from the at least one sensor data that represents the measure of the effect of the action to the material specimen.

15. The system of claim 12, further comprising a plurality of measurement apparatuses, each connected to the data acquisition unit.

\* \* \* \* \*